United States Patent
Cronin et al.

[11] Patent Number: 6,106,284
[45] Date of Patent: Aug. 22, 2000

[54] DENTAL CAST TRAY ASSEMBLY

[76] Inventors: Richard J. Cronin, 45 Cypress St., Medfield, Mass. 02052; Robert E. Vasile, 176 Myrtle St., Ashland, Mass. 01721

[21] Appl. No.: 09/231,154

[22] Filed: Jan. 15, 1999

[51] Int. Cl.[7] .................................................. A61C 19/00
[52] U.S. Cl. .............................................. 433/34; 433/54
[58] Field of Search ............................... 433/34 OR, 54, 433/60, 74

[56] References Cited

U.S. PATENT DOCUMENTS

| | | | |
|---|---|---|---|
| 4,035,916 | 7/1977 | Eveland | 433/60 |
| 4,139,943 | 2/1979 | Dragan | 433/74 |
| 4,265,619 | 5/1981 | Lucki et al. | 433/54 |
| 4,363,625 | 12/1982 | der Avanessian | 433/74 |
| 4,508,506 | 4/1985 | Jackson | 433/74 |
| 4,608,016 | 8/1986 | Zeiser | 433/74 |
| 4,767,330 | 8/1988 | Burger | 433/213 |
| 4,898,359 | 2/1990 | Gopon | 249/54 |
| 5,352,117 | 10/1994 | Silva | 433/34 |
| 5,393,227 | 2/1995 | Nooning | 433/74 |
| 5,506,095 | 4/1996 | Callne | 433/34 |

*Primary Examiner*—John J. Wilson
*Attorney, Agent, or Firm*—Kriegsman & Kriegsman

[57] ABSTRACT

In one embodiment of the present invention, a dental cast tray assembly used to form a dental cast model comprises a base and a tray removably mounted on the base. The base includes a top surface, a flat bottom surface, a front wall, a rear wall and a plurality of projections formed on its top surface in a non-recurring, random pattern. Each of the plurality of projections is generally cylindrically-shaped and includes a convex free end. The tray includes a top surface adapted to support the dental cast model, a flat bottom surface, a front wall, a rear wall, a retention bar formed on its top surface and a plurality of openings formed in its bottom surface in the same non-recurring, random pattern in which the plurality of projections are disposed on the base. Each of the plurality of openings is defined by four sidewalls and is generally hourglass shaped in lateral cross-section. Two of the four sidewalls which define each of the plurality of openings include an elongated rib. In use, the tray is mounted on the base such that the bottom surface of the tray abuts against the top surface of the base and so that the front wall of the tray is flush with the front wall of the base. With the tray mounted on the base, one projection in the base projects into an associated opening in the tray, the elongated ribs serving to retain each projection within its associated opening with limited retention.

22 Claims, 3 Drawing Sheets

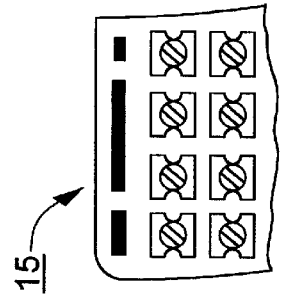
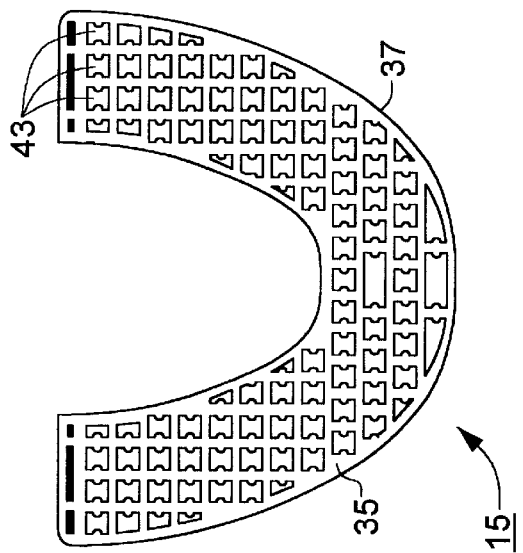
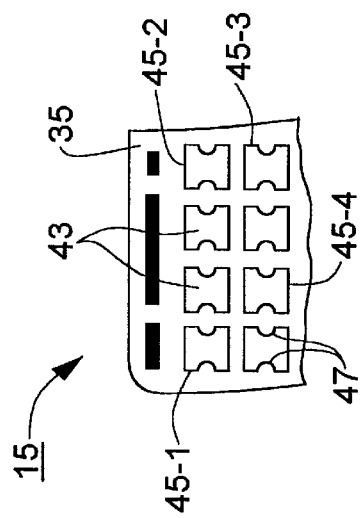
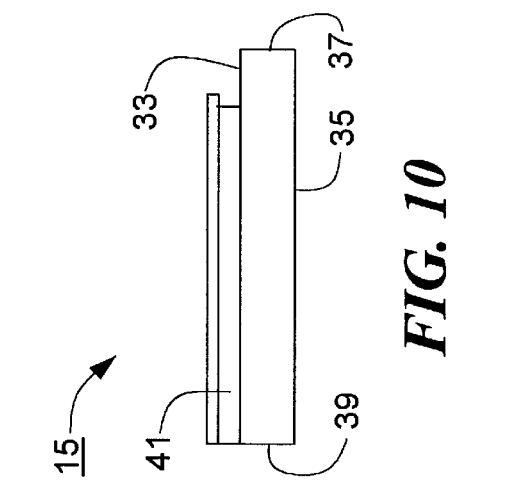
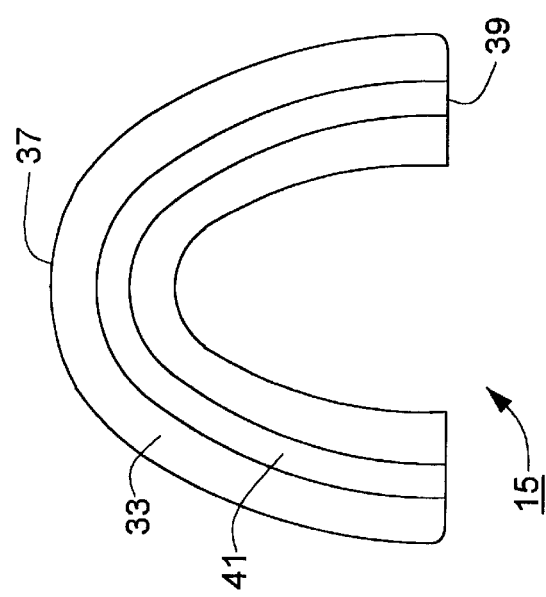
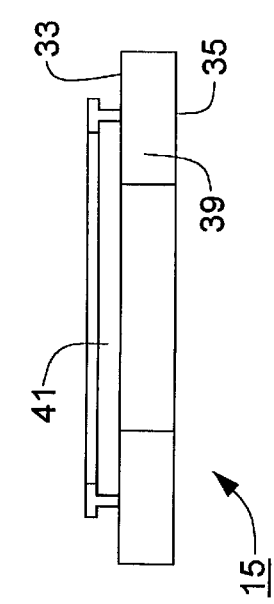

DENTAL CAST TRAY ASSEMBLY

BACKGROUND OF THE INVENTION

The present invention relates generally to the dental industry and, more particularly, to dental tools which are used in the production of dental cast models.

In the dental industry, technicians commonly use dental tools to construct a dental cast model of the mouth of a patient. The dental cast model comprises an upper jaw model and a lower jaw model which are typically affixed to one another by an articulator. An articulator is a device comprising upper and lower mounting platforms which are connected to the upper and lower jaw model elements. The articulator enables for centric, lateral and protrusive movement of the upper jaw model relative to the lower jaw model in order to closely simulate the relationships and the actual movement, or bite, of the mouth of the patient.

Various types of devices and procedures have been used in the art for creating a dental cast model.

One method for manufacturing dental cast models which is well known and commonly used in the art involves the execution of a molding process by a dental technician. Specifically, one or more plastic trays filled with impression material are used to create a negative impression of the full dental arch of a patient. The negative impression is then filled with a casting material, such as dental stone or epoxy. The impression tray is then inverted and mounted upon a pre-formed mounting device, such as a dental cast tray or base. After the casting material has had an opportunity to harden, the impression tray is removed so that the casting material forms a positive dental impression on the mounting surface.

Molded dental models are often used to manufacture crowns, bridges, inlays, dentures and other dental prosthetics outside of the mouth of the patient. The construction of dental prosthetics typically necessitates the ability to remove each individual model tooth, or die, from its spatial physical relationship to the remainder of the jaw model for the purpose of constructing accurate margins and contours. In the event that two or more individual units of bridgework are to be joined, it is necessary that the working model segments be accurately and repeatedly returned to their original relationships precisely as it or they existed prior to any cutting, separations or disassembly of the jaw model.

In order to effectively remove an individual model segment from the remainder of the dental model, the entire jaw model is typically removed from the mounting device and positioned upon a cutting surface. A cutting device, such as a saw, can then be used to separate the desired model teeth from the remainder of the dental model. After the technician has completed manufacture of the dental work, the dental model can be re-assembled onto the mounting device.

It should be noted that during the re-assembly of the dental cast model, it is essential that precise registration and desired occlusal alignment be maintained between the working model segments and the remainder of the molded jaw model.

In U.S. Pat. No. 5,506,095 to L. E. Callne, there is disclosed a dental tray cast subassembly for forming a dental cast model and for mounting to a dental articulator. The tray subassembly forms a channel shaped in a configuration of a human jaw to receive a mold material for forming a dental cast model. The channel further includes ribs for registering the model relative to the channel and a release mechanism for releasing the model from the channel. Further included is a platform for interconnecting with connectors for connecting the subassembly to an articulator.

Dental tray cast subassemblies of the type described above in Callne have been found to be undesirable because the casting material is used as an alignment device for returning the working model segments to the remainder of the molded jaw model. Specifically, the mold material adheres to and conforms with the material of the dental cast model and thereby serves as an alignment means for assuring proper registration of the dental cast model onto the dental articulator. However, because plasters are a relatively distortive material which can fragment over time, proper re-alignment of the working dental model back onto the remainder of the molded jaw model is not guaranteed, which is highly undesirable.

In U.S. Pat. No. 5,393,227 to W. H. Nooning there is disclosed a dental impression handling tool and method. The dental impression handling tool consists of two base structures shaped to approximate two opposite quadrants of a full dental arch, and two similarly-shaped inserts that snap fit into the base structures. Each base includes a wide, upward facing trough approximating the placement and curvature of teeth within a dental quadrant. The upper surface of each insert is attached to a positive dental mold by means of protrusions that extend from the top horizontal surface of the insert, the protrusions being encased within the mold material. Positive positional relationship is maintained between each base and its mating insert by the use of an interlocking and non-recurring geometric pattern that is carried by the internal vertical walls of the trough in the base, and by a matching geometric pattern that is carried by the outer vertical walls of two vertically downward extending ribs on the underside of the insert. A second deeper, narrower and centrally located trough is formed in each base. This second trough mates with a third center rib that protrudes from the bottom surface of each insert. The insert's center rib contains a retainer bead along both vertical side walls. This bead provides a snap-lock fit into a corresponding negative indentation formed along the vertical side walls of the center trough in each base. The center rib in each insert contains cylindrical cavities which allow the insertion of standard dental dowels or suitable substitutes.

Dental impression handling tools of the type described above in Nooning are undesirable in that the base comprises a slot into which debris can collect. As a result, often the insert will be unable to secure a proper fit within the base structure, thereby precluding proper alignment, which is highly undesirable.

SUMMARY OF THE INVENTION

It is an object of the present invention to provide a new and improved dental cast tray assembly which can be used to produce a dental cast model.

It is another object of the present invention to provide a dental cast tray assembly as described above which includes a base on which the dental cast model is removably mounted.

It is yet another object of the present invention to provide a dental cast tray assembly as described above which allows for repeated removal and replacement of the dental cast model on the base with proper alignment.

It is still another object of the present invention to provide a dental cast tray assembly as described above which can be mass produced, has a minimal number of parts, which is limited in size and can be very easily used.

Accordingly, there is provided a dental cast tray assembly used to form a dental cast model, comprising a base, said base having a top surface, a bottom surface, a front wall, a rear wall and a plurality of projections formed on the top surface of said base, and a tray removably mounted on said base, said tray having a top surface, a bottom surface, a front wall, a rear wall and a plurality of openings formed in the bottom surface of said tray, each of the plurality of openings being sized and shaped to receive an associated projection when said tray is mounted on said base.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration an embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate an embodiment of the present invention and, together with the description, serve to explain the principles of the invention. In the drawings wherein like reference numerals represent like parts:

FIG. 7 is a top view of the tray shown in FIG. 1;

FIG. 8 is a rear view of the tray shown in FIG. 1;

FIG. 9 is a bottom view of the tray shown in FIG. 1;

FIG. 10 is a side view of the tray shown in FIG. 1;

FIG. 11 is an enlarged, fragmentary, bottom view of the tray shown in FIG. 9; and FIG. 12 is an enlarged, fragmentary, bottom view of the tray shown in FIG. 11, the tray being shown with a projection on the base disposed within an associated opening in the tray, the projection being shown in cross-section.

DETAILED DESCRIPTION OF A PREFERRED EMBODIMENT

Figure 2:
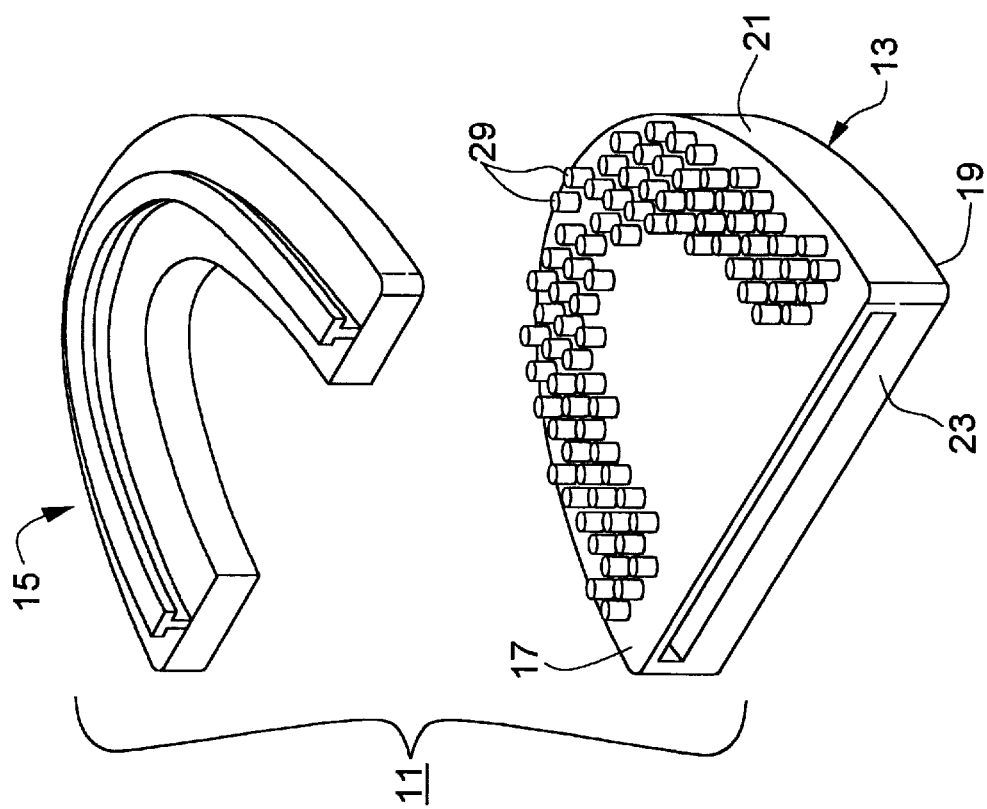
FIG. 2 is an exploded perspective view of the dental cast tray assembly shown in FIG. 1.

Referring now to the drawings, there is shown a dental cast tray assembly constructed according to the teachings of the present invention, the dental cast tray assembly being represented generally by reference numeral 11. As will be described further in detail below, dental cast tray assembly 11 can be used to form an upper or lower jaw dental cast model 12. Accordingly, a pair of dental cast tray assemblies 11 can be supported by an articulator to create a positive dental cast model of the entire mouth of a patient which can then be used in the dental industry to manufacture crowns, bridges or other dental prosthetics.

Dental cast tray assembly 11 comprises a base 13 and a tray 15 removably mounted on base 13. Both base 13 and tray 15 are made of a plastic material which retains its rigidity in thin-wall construction and which is able to be easily manually cut by a saw blade. Preferably, base 13 and tray 15 are manufactured of a glass filled nylon plastic that will withstand a temperature of approximately 270 degrees.

Referring now to FIGS. 3–6, base 13 comprises a top surface 17, a bottom surface 19, an arcuate front wall 21 and a rear wall 23. Bottom surface 19 comprises a plurality of square-shaped recesses 25 formed therein to reduce the amount of plastic material required to manufacture base 13. It should be noted that bottom surface 19 is generally flat so as to enable base 13 to be placed on a working surface in a stable position.

Rear wall 23 is generally flat and comprises an elongated recess 27 formed therein. Elongated recess 27 is sized and shaped to receive a hinge for an articulator. As such, a pair of dental cast tray assemblies 11 can be supported by an articulator to create a positive dental cast model of the entire mouth of a patient, wherein an upper dental cast tray assembly is capable of centric, lateral and protrusive movement relative to a lower dental cast tray assembly.

Base 13 further comprises a plurality of generally cylindrically-shaped projections 29 which are formed on and protrude out from top surface 17. Each projection 29 has an approximate length $L_1$ of 0.1 inches and includes an outwardly curved free end 31. As shown in FIG. 2, projections 29 are patterned in a random order so as to ensure accurate alignment of tray 15 on base 13, as will be described further in detail below.

Referring now to FIGS. 7–10, tray 15 is a generally U-shaped, unitary member which is shaped to approximate a full dental arch. Tray 15 comprises a top surface 33, a generally flat bottom surface 35, an arcuate front wall 37 and a rear wall 39.

Tray 15 further comprises a retention bar 41 formed on top surface 33. Retention bar 41 is an elongated, arcuate member which is T-shaped in lateral cross-section. As will be described further in detail below, top surface 33 is adapted to support and receive a quantity of casting material formed from a negative dental impression of the patient which can then be used to form dental cast model 12 which is retained by retention bar 41. Specifically, retention bar 41 is permanently bonded to the casting material to prevent vertical separation, as well as longitudinal slippage of dental cast model 12 relative to tray 15.

Bottom surface 35 of tray 15 comprises a plurality of openings 43 which are patterned in the identical formation as projections 29 are patterned on base 13. As such, with tray 15 accurately mounted on base 13, one projection 29 will protrude into an associated opening 43. It should be noted that accurate positive positional relationship is maintained between tray 15 and base 13 by the use of the interlocking and non-recurring geometric pattern of projections 29 on base 13 which matches the pattern of openings 43 on tray 15. Due to the irregular, non-repeating patterns, there is only one way or position in which tray 15 is mountable on base 13, openings 43 and projections 29 thereby acting an indexing function for proper alignment.

As shown in FIG. 11, each opening 43 formed in bottom surface 35 of tray 15 is defined by first, second, third and fourth sidewalls 45-1 through 45-4. Opposite sidewalls 45-1 and 45-3 each comprise an elongated rib 47 which protrudes slightly into opening 43. As such, sidewalls 45 are disposed so as to create an opening 43 which is generally hourglass-shaped in lateral cross-section. As will be described further in detail below, ribs 47 serve to retain one projection 29 within its associated opening 43 with limited retention so as to create a snug, yet removable, fit, as shown in FIG. 12.

Figure 1:
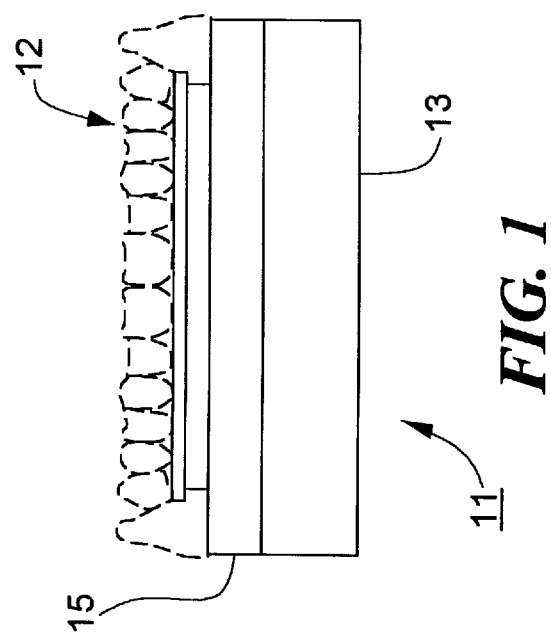
FIG. 1 is a front view of a dental cast tray assembly constructed according to the teachings of the present invention, the dental cast tray assembly being shown with a positive dental cast model formed thereon in phantom.
Figure 5:
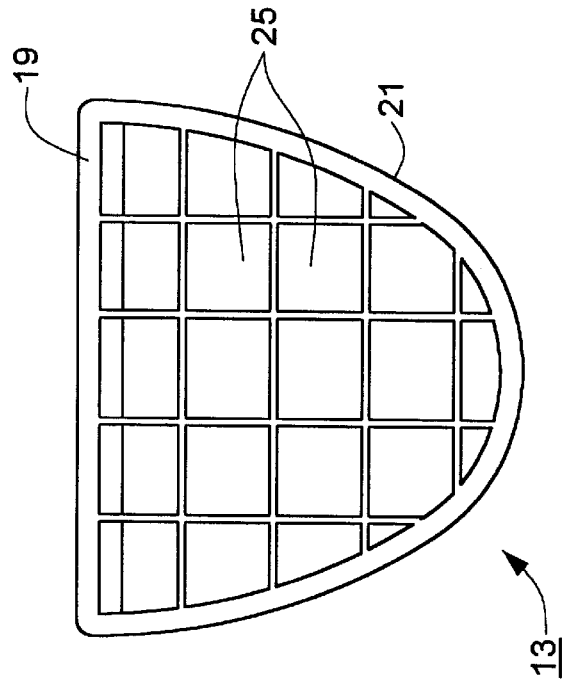
FIG. 5 is a bottom view of the base shown in FIG. 1.
Figure 6:
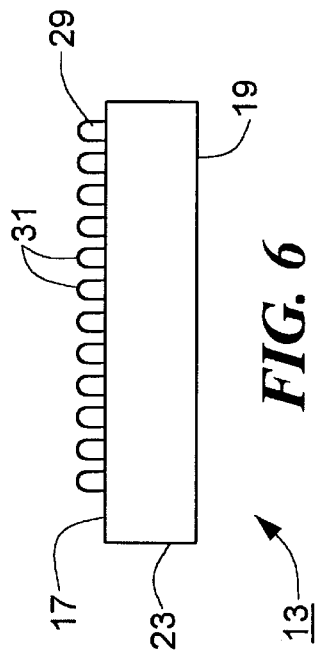
FIG. 6 is a side view of the base shown in FIG. 1.
Figure 3:
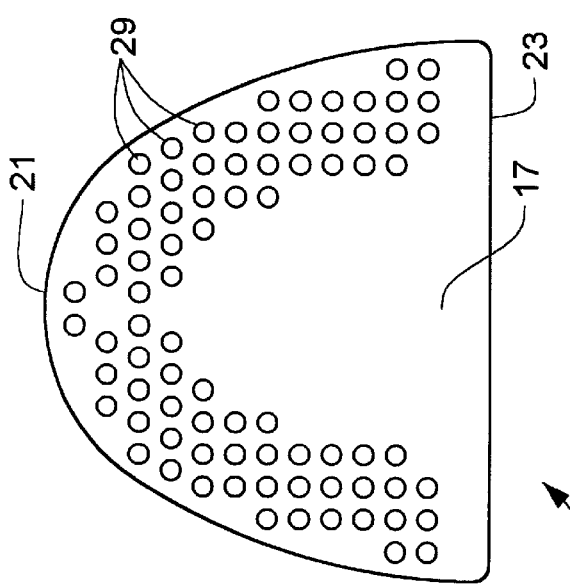
FIG. 3 is a top view of the base shown in FIG. 1.
Figure 4:
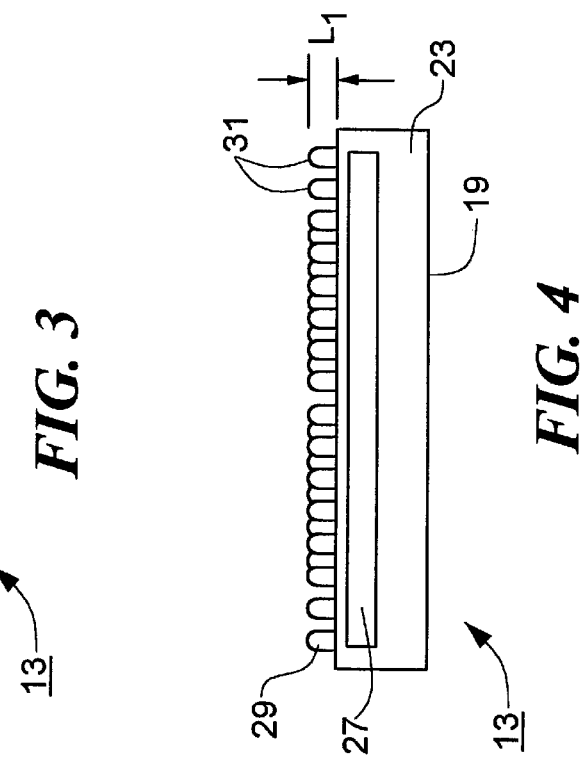
FIG. 4 is a rear view of the base shown in FIG. 1.

In use, dental cast tray assembly 11 can be used to manufacture dental cast model 12 in the following manner. Tray 15 is mounted on base 13 so that bottom surface 35 of tray 15 abuts against top surface 17 of base 13 in a plastic-to-plastic relation and so that arcuate front wall 37 of tray 15 is flush with arcuate front wall 21 of base 13, as shown in FIG. 1. It should be noted that a plastic to plastic relation ensures that there is a no possibility of distortion, thereby guaranteeing proper mounting of tray 15 on base 13. Furthermore, because openings 43 are disposed on bottom surface 35 of tray 15 rather than on top surface 17 of base 13, debris is less likely to fall into openings 43 and thereby prevent the proper abutment of tray 15 onto base 13. With tray 15 accurately mounted on base 13, one projection 29 will protrude into an associated opening 43. As noted above, the irregular, non-repeating patterns of projections 29 and openings 43 serve to properly align tray 15 on base 13.

A rubber based material is used to take a negative impression of the upper or lower jaw of the mouth of a patient. A thick plaster, or casting, material is then deposited within the negative impression. With the plaster material disposed therewithin, the negative impression is flipped over onto top surface 33 of tray 15.

After the plaster material hardens approximately ½ hour later, the rubber impression is peeled off tray 15, thereby leaving a positive plaster cast model 12 which is permanently attached to tray 15 by the interlocking of the hardened mold material of model 12 onto retention bar 41. Dental cast model 12 can then be used in the dental industry to manufacture crowns, bridges or other dental prosthetics.

Construction of a particular dental prosthetic begins by removing tray 15 from base 13. As can be appreciated, due to the limited retention of projections 29 within its associated openings 43 by ribs 47, tray 15 can be easily removed from base 13. Removed from base 13, tray 15 is placed upon a flat cutting surface. Because bottom surface 35 of tray 15 is flat, tray 15 is stable when positioned upon the cutting surface.

With tray 15 positioned on the cutting surface, construction of the dental prosthetic requires isolation of the tooth or teeth for which the prosthesis will be constructed from the remaining teeth. This is accomplished by sawing down through dental cast model 12 and tray 15 on both sides of the teeth which will receive the prosthesis. Once the appropriate saw cuts have been made, the section of teeth which was isolated is removed to allow ease of manipulation during construction of the prosthesis.

Upon completion of the prosthesis, the isolated teeth, as well as the remaining untreated teeth, are remounted onto base 13 in the exact alignment prior to cutting, due to the irregular, non-repeating patterns of projections 29 and openings 43. It should be noted that the convex shape of outwardly curved free end 31 of each projection 29 greatly facilitates the process of remounting tray 15 onto base 13. With tray 15 having been remounted on base 13, the dental technician is able to sufficiently inspect the precise relation of the prosthesis relative to the entire dental cast model 12.

The embodiment of the present invention described above is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A dental cast tray assembly used to form a dental cast model, comprising:
    a. a base, said base having a top surface, a bottom surface, a front wall, a rear wall and a plurality of projections formed on the top surface of said base; and
    b. a substantially U-shaped tray removably mounted on said base, said tray having a top surface, a generally flat bottom surface, a front wall, a rear wall and a plurality of openings formed in the bottom surface of said tray, each of the plurality of openings being sized and shaped to receive an associated projection when said tray is mounted on said base.

2. The dental cast tray assembly of claim 1 wherein the top surface of said tray is adapted to support the dental cast model.

3. The dental cast tray assembly of claim 2 wherein the bottom surface of said tray abuts against the top surface of said base when said tray is mounted on said base.

4. The dental cast tray assembly of claim 3 wherein each of the plurality of openings in said tray is defined by a plurality of sidewalls.

5. A dental cast tray assembly used to form a dental cast model, comprising:
    a. a base, said base having a top surface, a bottom surface, a front wall, a rear wall and a plurality of projections formed on the top surface of said base, said base including a slot for use in attaching the dental cast tray assembly to an articulator; and
    b. a tray removably mounted on said base, said tray having a top surface, a generally flat bottom surface, a front wall, a rear wall and a plurality of openings formed in the bottom surface of said tray, each of the plurality of openings being sized and shaped to receive an associated projection when said tray is mounted on said base.

6. A dental cast tray assembly used to form a dental cast model, comprising:
    a. a base, said base having a top surface, a bottom surface, a front wall, a rear wall and a plurality of projections formed on the top surface of said base; and
    b. a tray removably mounted on said base, said tray having a top surface adapted to support the dental cast model, a generally flat bottom surface, a front wall, a rear wall and a plurality of openings formed in the bottom surface of said tray, each of the plurality of openings being sized and shaped to receive an associated projection when said tray is mounted on said base, the bottom surface of said tray abutting against the top surface of said base when said tray is mounted on said base;
    c. wherein each of the plurality of openings in said tray is defined by a plurality of sidewalls, at least one of the plurality of sidewalls which define each of the plurality of openings comprising an inwardly protruding rib.

7. The dental cast tray assembly of claim 6 wherein each of the plurality of openings is generally hourglass-shaped in lateral cross-section.

8. The dental cast tray assembly of claim 7 wherein each of the plurality of projections on said base is generally cylindrically-shaped and includes an convex free end.

9. The dental cast tray assembly of claim 8 wherein the plurality of projections are disposed on said base in a non-recurring, random pattern.

10. The dental cast tray assembly of claim 9 wherein the plurality of openings are disposed on said tray in the same non-recurring, random pattern in which the plurality of projections are disposed on said base so that one of the plurality of projections aligns with and protrudes into one of the plurality of openings when said tray is mounted on said base.

11. The dental cast tray assembly of claim 10 wherein the front wall of said tray is flush with the front wall of said base when said tray is mounted on said base.

12. The dental cast tray assembly of claim 11 wherein said tray comprises a retention bar formed on its top surface.

13. The dental cast tray assembly of claim 12 wherein each of the plurality of projections has an approximate length of 0.1 inches.

14. The dental cast tray assembly of claim 13 wherein the bottom surface of said base is flat.

15. The dental cast tray assembly of claim 14 wherein said retention bar is generally T-shaped in lateral cross-section.

16. The dental cast tray assembly of claim 15 wherein the bottom surface of said base comprises a plurality of recesses.

17. The dental cast tray assembly of claim 16 wherein said base and tray are constructed of a plastic material.

18. The dental cast tray assembly of claim 17 wherein said base and tray are constructed of a glass filled nylon plastic capable of withstanding a temperature of approximately 270 degrees.

19. The dental cast tray assembly of claim 18 wherein the rear wall of said base is generally flat an includes an elongated recess which is sized and shaped to receive a hinge for an articulator.

20. A dental cast tray assembly used to form a dental cast model, comprising:
   a. a base, said base having a top surface, a bottom surface, a front wall and a rear wall;
   b. a tray removably mounted on said base, said tray having a top surface, a bottom surface, a front wall and a rear wall;
   c. a plurality of projections formed on one of said base and said tray; and
   d. a plurality of openings formed on the other one of said base and said tray, each of the plurality of openings being sized and shaped to receive an associated projection when said tray is mounted on said base, wherein each of the plurality of openings is defined by a plurality of sidewalls, at least one of the plurality of sidewalls comprising an inwardly protruding rib.

21. A dental cast tray assembly used to form a dental cast model, comprising:
   a. a base, said base having a top surface, a bottom surface, a front wall, a rear wall and a plurality of projections formed on the top surface of said base; and
   b. a tray removably mounted on said base, said tray having a top surface, a generally flat bottom surface, a front wall, a rear wall and a plurality of openings formed in the bottom surface of said tray, each of the plurality of openings being sized and shaped to receive an associated projection when said tray is mounted on said base, said tray having a retention bar formed on the top surface which is adapted to support the dental cast model.

22. A dental cast tray assembly used to form a dental cast model, comprising:
   a. a base, said base having a top surface, a bottom surface, a front wall, a rear wall and a plurality of projections formed on the top surface of said base; and
   b. a tray removably mounted on said base, said tray having a top surface, a generally flat bottom surface, a front wall, a rear wall and a plurality of openings formed in the bottom surface of said tray, each of the plurality of openings being sized and shaped to receive an associated projection when said tray is mounted on said base;
   c. wherein a portion of the top surface of said tray is adapted to support the dental cast model, the plurality of openings formed in the bottom surface of said tray being disposed directly beneath the portion of the top surface of said tray which is adapted to support the dental cast model.

* * * * *